United States Patent [19]

Domeier

[11] Patent Number: 4,654,407
[45] Date of Patent: Mar. 31, 1987

[54] AROMATIC BISMALEIMIDE AND PREPREG RESIN THEREFROM

[75] Inventor: Linda A. Domeier, Somerville, N.J.

[73] Assignee: Amoco Corporation, Chicago, Ill.

[21] Appl. No.: 761,432

[22] Filed: Aug. 2, 1985

[51] Int. Cl.[4] .............................. C08F 122/40
[52] U.S. Cl. ................................. 526/262; 528/322; 548/407; 548/521
[58] Field of Search ........................ 526/262; 528/322; 548/521, 407

[56] References Cited

U.S. PATENT DOCUMENTS

| | | | |
|---|---|---|---|
| 3,627,780 | 12/1971 | Bonnard et al. | 548/521 |
| 3,839,287 | 10/1974 | Kwiatkowski et al. | 548/521 |
| 4,464,520 | 8/1984 | Adams et al. | 526/262 |
| 4,564,683 | 1/1986 | Adams et al. | 526/262 |
| 4,568,733 | 2/1986 | Parker et al. | 526/262 |

FOREIGN PATENT DOCUMENTS 8174361 4/1982 Japan .

Primary Examiner—Harold D. Anderson
Attorney, Agent, or Firm—William H. Magidson; Ralph C. Medhurst; William T. McClain

[57] ABSTRACT

Described herein are novel bismaleimides and prepregable resin compositions comprising these bismaleimides and one or more liquid coreactants and optionally, one or more other additives. The novel bismaleimides, such as alpha, alpha-bis-(4-maleimidophenyl)-meta-diisopropylbenzene, are characterized by the presence of three aromatic rings in the molecular structure and in some respects optimize the desirable characteristics of the one or two and four aromatic ring-containing bismaleimides in resins prepared therefrom.

10 Claims, No Drawings

AROMATIC BISMALEIMIDE AND PREPREG RESIN THEREFROM

FIELD OF THE INVENTION

This invention relates in general to novel bismaleimide compositions. In one aspect, this invention is directed to novel aromatic bismaleimides, such as alpha, alpha'-bis (4-maleimidophenyl)-meta-diisopropylbenzene and alpha, alpha'-bis(4-maleimidophenyl)-paradiisopropylbenzene. In a further aspect, the present invention relates to the use of the novel bismaleimide compositions in the preparation of prepreg resins and the resins prepared therefrom.

BACKGROUND OF THE INVENTION

Advanced composites are high strength, high modulus materials which are finding increasing use as structural components in aircraft, automotive, and sporting goods applications. Typically they comprise structural fibers such as carbon fibers in the form of woven cloth or continuous filaments embedded in a thermosetting resin matrix.

Most advanced composites are fabricated from prepreg, a ready-to-mold sheet of reinforcement impregnated with uncured or partially cured resin. Resin systems containing an epoxide resin and aromatic amine hardener are often used in prepreg since they possess the balance of properties required for this composite fabrication process. State-of-the-art epoxy/carbon fiber composites have high compressive strengths, good fatigue characteristics, and low shrinkage during cure. However, most epoxy formulations absorb moisture which reduces their high temperature properties. As a result they are not suitable for use at 350° F. or greater in a moisture saturated condition. There is therefore a need for resin systems which afford composites which can retain a high level of properties at 350° F. under such moisture saturated conditions.

Most prepreg resins designed for use at 350° F. are made by combining bismaleimides of Formula I with liquid coreactants containing other reactive groups such as amines, epoxides, cyanates or comonomers containing —CH=CH$_2$, >C=CH$_2$, or —CH=CH— groups which can react or polymerize with the carbon-carbon double bonds of the maleimide groups.

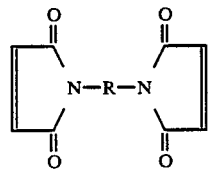

In common bismaleimides, R is the residue of an aromatic diamine such as methylene dianiline or m-phenylene diamine.

However prior to the present invention the available aromatic bismaleimides usually contained one, two or four aromatic rings in the structure. Few, if any, bismaleimides have been reported containing three aromatic rings in the molecule, primarily due to a lack of available diamine precursors containing three aromatic rings. Accordingly, it was found that novel bismaleimides could be prepared which contained three aromatic rings in the structure and that these novel bismaleimides, in some respects, optimized the desirable characteristics of both the one or two and four aromatic ring-containing bismaleimides.

For example, bismaleimides containing one or two aromatic rings tend to give formulations which are characterized by high water absorption, high Tg and low toughness. Equivalent formulations in which the aromatic nucleus has four, or more aromatic rings, tend to be characterized by lower water absorption, low Tg, and higher toughness. It is desirable to provide resins characterized by high Tg, low water absorption, and high toughness.

SUMMARY OF THE INVENTION

This invention is directed to:
(i) bismaleimides of formula (II),

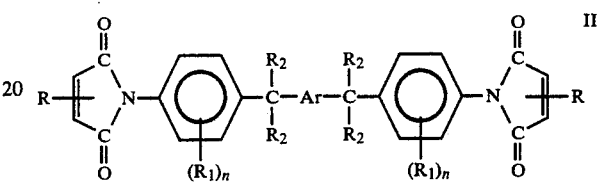

wherein Ar, R, R$_1$, and R$_2$ are as hereinafter defined, and (ii) prepregable resin compositions comprising II and one or more liquid coreactants and optionally, other additives.

These compositions may optionally contain a structural fiber.

DETAILED DESCRIPTION OF THE INVENTION

As indicated above, the present invention is directed to novel aromatic bismaleimides of formula (II) and prepreg resins prepared therefrom. The novel bismaleimides are those wherein Ar represents a single or fused aromatic nucleus, preferably a hydrocarbon aromatic nucleus of up to 10 carbon atoms, which may optionally contain one or more R or R$_1$ substituents. R and R$_1$ individually represent alkyl or halogen groups, and R$_2$ represents alkyl groups of from 1-12 carbon atoms and n has a value of from 0 to 4. Preferred bismaleimides which can be prepared by the teachings of this invention are those wherein Ar represents a substituted or unsubstituted meta-or para-phenylene group and R and R$_1$ represent lower alkyl groups of from 1 to 4 carbon atoms or halogen, preferably bromine and chlorine, and R$_2$ is methyl.

In general formula II, it is also meant to include compositions wherein up to 50% of the maleimide or substituted maleimide groups have been replaced by other terminal imide groups such as

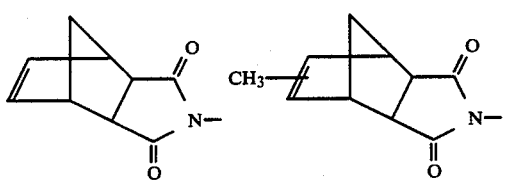

succinimide, phthalimide, or substituted succinimide, or phthalimide groups.

Particularly preferred bismaleimides are those represented by the formulas:

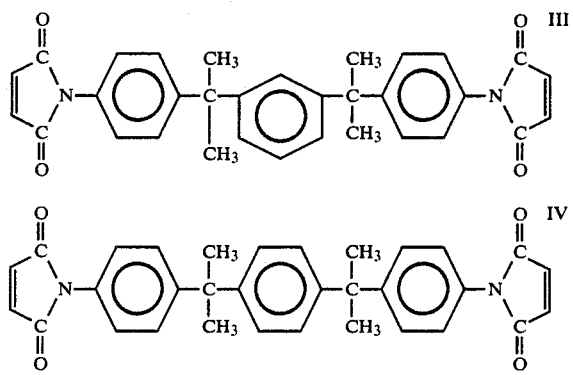

Aromatic bismaleimides encompassed by formula II above, also include those wherein Ar represents naphthylene or substituted naphthylene with from 0 to 6 R or $R_1$ substituents.

Also encompassed by (i) are blends of one or more of the bismaleimides of formula II and also blends which include up to 50% of bismaleimides other than those of formula II. Particularly useful are blends of the bismaleimides of formulas III and IV.

As indicated above, the bismaleimides of the present invention are particularly useful in the preparation of prepreg resins having optimal levels of low water uptake, high Tg and good toughness. The preferred bismaleimides also provide a wide range of solubility properties and melting characteristics due to the presence of para- and meta-linkages in the central aromatic nucleus. Such diversity is useful in the formulation of bismaleimide prepreg resins to impart high temperature performance, moisture resistance, toughness and processability.

The bismaleimides of the present invention can be prepared by condensing certain aromatic diamines, as hereinafter defined with maleic anhydride, substituted maleic anhydrides, or other anhydrides under a variety of conditions.

For example, the novel aromatic bismaleimides can be prepared by reacting maleic anhydride with an alpha, alpha'-bis(4-aminophenyl)-meta/para diisopropyl benzene in accordance with the following equation:

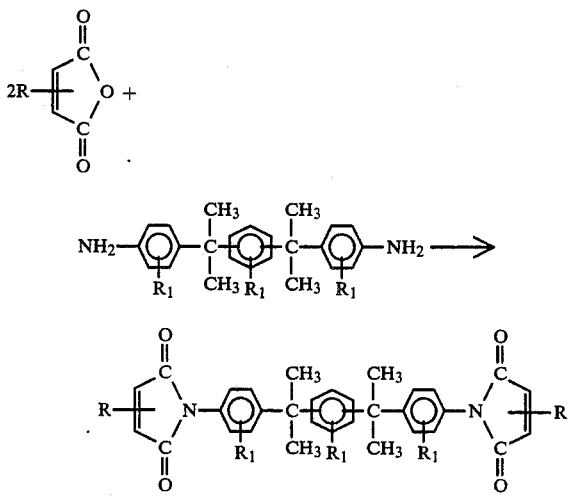

wherein R and $R_1$ are as indicated above.

The diamine starting materials of this invention may be prepared by one or more methods disclosed in the literature. For example, one general route for preparing the diamines involves the reaction of alpha, alpha' dihydroxy-para-diisopropyl benzene with aniline in the presence of an acidic alumina catalyst and heating the mixture to 160°–220° C. to give alpha, alpha'-bis(4-amino)-para-diisopropylbenzene. Details of the method are reported by H. J. Buysch et al. in German Offen. DE No. 2,111,194 published Sept. 14, 1972. A similar method is also disclosed for the preparation of substituted aminoaryl compounds and derivatives in Netherlands patent application No. 6,408,539 of Jan. 20, 1965 by Allied Chemical Corp.

Another general method which can also be employed for the preparation of the diamine starting materials involves the reaction of a diisopropenylbenzene with an aniline hydrochloride under a nitrogen atmosphere and at temperatures of from 180°–200° C. as disclosed in U.S. Pat. No. 3,206,152 assigned to Farbenfabriken Bayer, A.G. A further method for preparing the diamines starting from diisopropenylbenzene is disclosed in U.S. Pat. No. 3,365,347 which issued Jan. 23, 1968 to Allied Chemical Corp.

Certain of the diamine starting materials are available commercially, such as for example, alpha, alpha'-bis-(4-aminophenyl)-meta-diisopropylbenzene and alpha, alpha'-bis(4-aminoiphenyl)-para-diisopropylbenzene which can be obtained from Mitsui Petrochemicals Industries Ltd, Japan, having an office at 200 Park Avenue, New York, N.Y. 10017.

As indicated above, the novel aromatic bismaleimides of the present invention are particularly suited for use in the preparation of prepregable resin compositions. These compositions are comprised of the novel bismaleimide and one or more liquid coreactants and optionally, other additives.

The liquid coreactants in composition (ii) of this invention include N-vinyl-2-pyrrolidinone, N-vinyl caprolactam, ethylene glycol dimethacrylate, diethylene glycol dimethacrylate, trimethylolpropane triacrylate, trimethylolpropane trimethacrylate, pentaerythritol triacrylate, pentaerythritol tetraacrylate, pentaerythritol tetramethacrylate, triallyl isocyanurate, diallyl phthalate, o,o'-diallyl bisphenol A, Eugenol, triallyl trimellitate, divinyl benzene, dicyclopentadienyl acrylate, dicyclopentadienyloxyethyl acrylate, vinylcyclohexene monoepoxide, 1,4-butanediol divinyl ether, 1,4-dihydroxy-2-butene, styrene, alpha methyl styrene, chlorostyrene, p-phenylstyrene, p-methylstyrene, t-butylstyrene, phenyl vinyl ether, unsaturated polyesters, vinyl ester resins, and the like. These comonomers are characterized by the presence of one or more —CH=$CH_2$, >C=$CH_2$, or —CH=CH— groups which can polymerize or react with the maleimide groups of the bismaleimide.

Other liquid coreactants include epoxy resins which contain one or more epoxy groups having the following formula:

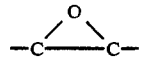

The epoxy groups can be terminal epoxy groups or internal epoxy groups. The epoxides are of two general types: polyglycidyl compounds or products derived from epoxidation of dienes or polyenes. Polyglycidyl compounds contain a plurality of 1,2-epoxide groups derived from the reaction of a polyfunctional active hydrogen containing compound with an excess of an epihalohydrin under basic conditions. When the active hydrogen compound is a polyhydric alcohol phenol, the resulting epoxide resin contains glycidyl ether groups. A preferred group of polyglycidyl compounds are made via condensation reactions with 2,2-bis(4-hydroxyphenyl)propane, also known as bisphenol A, and have structures such as V.

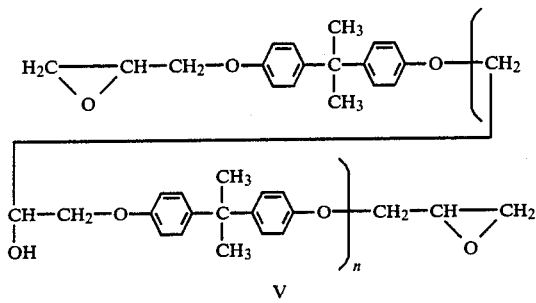

V where n has a value from about 0 to about 15. These epoxides are bisphenol-A epoxy resins. They are available commercially under the trade names such as "Epon 828," "Epon 1001", and "Epon 1009" from Shell Chemical Co., and as "DER 331", and "DER 334" from Dow Chemical Co. The most preferred bisphenol A epoxy resins have an "n" value between 0 and 10.

Polyepoxides which are polyglycidyl ethers of 4,4'-dihydroxydiphenyl methane, 4,4'-dihydroxydiphenyl sulfone, 4,4'-biphenol, 4,4'-dihydroxydiphenyl sulfide, phenolphthalein, resorcinol, 4,2'-biphenol, or tris(4-hydroxyphenyl)methane and the like, are useful in this invention. In addition, EPON 1031 (a tetraglycidyl derivative of 1,1,2,2-tetrakis(hydroxyphenyl)ethane from Shell Chemical Company), and Apogen 101, (a methylolated bisphenol A resin from Schaefer Chemical Co.) may also be used. Halogenated polyglycidyl compounds such as D.E.R. 580 (a brominated bisphenol A epoxy resin from Dow Chemical Company) are also useful. Other suitable epoxy resins include polyepoxides prepared from polyols such as pentaerythritol, glycerol, butanediol or trimethylolpropane and an epihalohydrin.

Polyglycidyl derivatives of phenol-formaldehyde novolaks such as (VI) where n=0.1 to 8 and cresol-formaldehyde novolaks such as VII where n=0.1 to 8 are also usable.

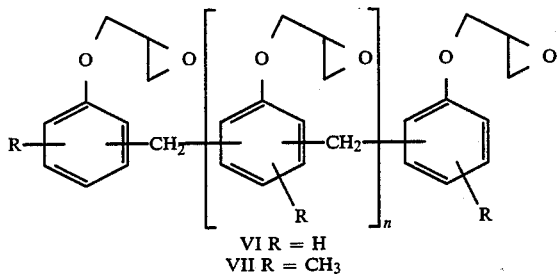

VI R = H
VII R = CH$_3$

The former are commercially available as D.E.N 431, D.E.N. 438, and D.E.N. 485 from Dow Chemical Company. The latter are available as, for example, ECN 1235, ECN 1273, and ECN 1299 (obtained from Ciba-Geigy Corporation, Ardsley, NY). Other epoxidized novolaks such as SU-8 (obtained from Celanese Polymer Specialties Company, Louisville, KY.) are also suitable.

Other polyfunctional active hydrogen compounds besides phenols and alcohols may be used to prepare the polyglycidyl adducts of this invention. They include amines, aminoalcohols and polycarboxylic acids.

Adducts derived from amines include N,N-diglycidyl aniline, N,N-diglycidyl toluidine, N,N,N',N'-tetraglycidylxylylene diamine, (i.e., VIII) N,N,N',N'-tetraglycidyl-bis(methylamino)cyclohexane (i.e. IX), N,N,N',N'-tetraglycidyl-4,4'-diaminodiphenyl methane, (i.e. X) N,N,N',N'-tetraglycidyl-3,3'-diaminodiphenyl sulfone, and N,N'-dimethyl-N,N'-diglycidyl-4,4'-diaminodiphenyl methane. Commercially available resins of this type include Glyamine 135 and Glyamine 125 (obtained from F.I.C. Corporation, San Francisco, CA.), Araldite MY-720 (obtained from Ciba Geigy Corporation) and PGA-X and PGA-C (obtained from The Sherwin-Williams Co., Chicago, Ill.).

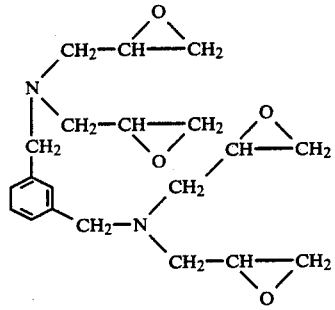

VIII

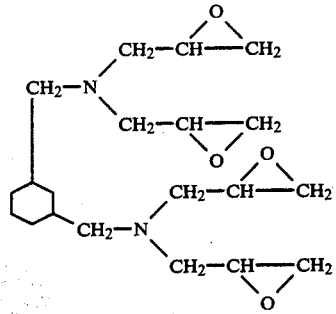

IX

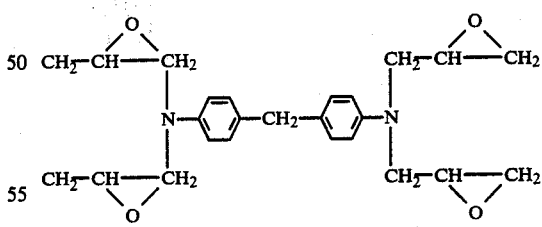

(X)

Suitable polyglycidyl adducts derived from aminoalcohols include O,N,N-triglycidyl-4-aminophenol, available as Araldite 0500 or Araldite 0510 (obtained from Ciba Geigy Corporation) and O,N,N-triglycidyl-3-aminophenol (available as Glyamine 115 from F.I.C. Corporation).

Also suitable for use herein are the glycidyl esters of carboxylic acids. Such glycidyl esters include, for example, diglycidyl phthalate, diglycidyl terephthalate, diglycidyl isophthalate, and diglycidyl adipate. There may also be used polyepoxides such as triglycidyl cyanurates and isocyanurates, N,N-diglycidyl oxamides, N,N'-diglycidyl derivatives of hydantoins such as "XB 2793" (obtained from Ciba Geigy Corporation), diglycidyl esters of cycloaliphatic dicarboxylic acids, and polyglycidyl thioethers of polythiols.

Other epoxy-containing materials are copolymers of acrylic acid esters of glycidol such as glycidyl acrylate and glycidyl methacrylate with one or more copolymerizable vinyl compounds. Examples of such copolymers are 1:1 styrene-glycidyl methacrylate, 1:1 methyl methacrylate-glycidyl acrylate and 62.5:24:13.5 methyl methacrylate:ethyl acrylate:glycidyl methacrylate.

Silicone resins containing epoxy functionality, e.g., 2,4,6,8,10-pentakis[3-(2,3-epoxypropoxy)propyl]-2,4,6,8,10-pentamethylcyclopentasiloxane and the diglycidyl ether of 1,3-bis-(3-hydroxypropyl)tetramethyldisiloxane) are also usable.

The second group of epoxy resins is prepared by epoxidation of dienes or polyenes. Resins of this type include bis(2,3-epoxycyclopentyl)ether, XIII,

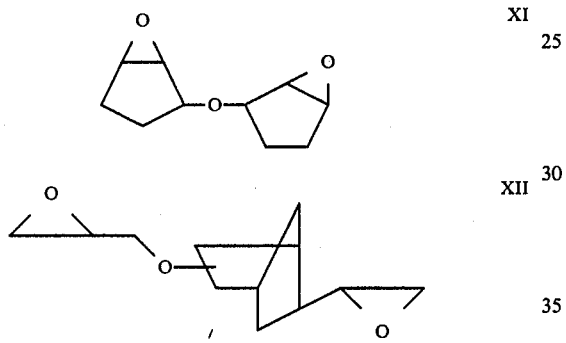

XI

XII reaction products of (XI) with ethylene glycol which are described in U.S. Pat. No. 3,398,102, 5(6)-glycidyl-2-(1,2-epoxyethyl)bicyclo[2.2.1]heptane, XII and dicyclopentadiene diepoxide. Commercial examples of these epoxides include vinylcyclohexene dioxide, e.g., "ERL-4206" (obtained from Union Carbide Corp.), 3,4-epoxycyclohexylmethyl 3,4-epoxycyclohexane carboxylate, e.g., "ERL-4221" (obtained from Union Carbide Corp.), 3,4-epoxy-6-methylcyclohexylmethyl 3,4-epoxy-6-methylcyclohexane carboxylate, e.g., "ERL-4201" (obtained from Union Carbide Corp.), bis(3,4-epoxy-6-methylcyclohexylmethyl)adipate, e.g., "ERL-4289" (obtained from Union Carbide Corp.), dipentene dioxide, e.g., "ERL-4269" (obtained from Union Carbide Corp.) 2-(3,4-epoxycyclohexyl-5,5-spiro-3,4-epoxy)cyclohexanemetadioxane, e.g., "ERL-4234" (obtained from Union Carbide Corp.) and epoxidized polybutadiene, e.g., "Oxiron 2001" (obtained from FMC Corp.)

Other suitable cycloaliphatic epoxides include those described in U.S. Pat. Nos. 2,750,395; 2,890,194; and 3,318,822 which are incorporated herein by reference, and the following:

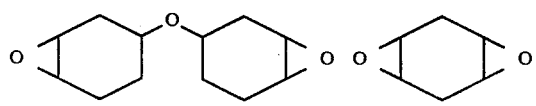

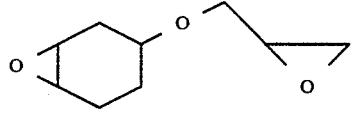

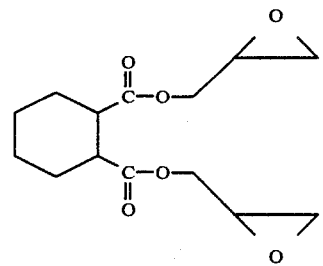

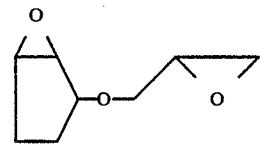

Other suitable epoxides include:

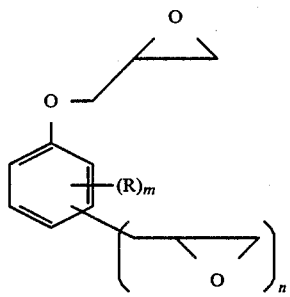

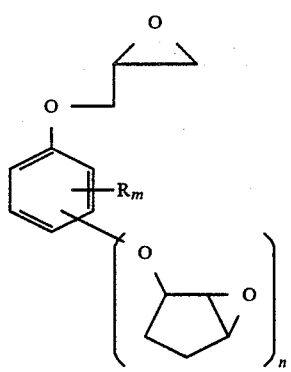

where n is 1 to 4, m is (5−n), and R is H, halogen or $C_1$ to $C_4$ alkyl.

Also included as epoxy modifers are epoxy-terminated thermoplastic polymers such as epoxy-terminated polysulfone and other similar resins.

If epoxy resins are used, it is desirable to add an aromatic diamine to the formulation. The diamine should have a low level of reactivity with epoxy resin and the bismaleimide at room temperature. Suitable diamines include 4,4'-diaminodiphenyl sulfone, 3,3'-diaminodiphenyl sulfone, 3,4'-diaminobenzophenone, 4,4'-diaminobenzophenone, 4,4'-bis(3-aminophenoxy)diphenyl sulfone, the diamino starting materials employed in the preparation of the novel bismaleimides of this invention, e.g., α,α'-bis(4-aminodiphenyl)-meta-diisopropylbenzene, and the like.

A stoichimetry of 0.1 to 1.0 equivalents of —NH per equivalent of (1,2-epoxide group plus maleimide group) may be used.

Diamines may also be used even if no epoxy is used. In this case the diamines may react during the cure cycle with the bismaleimides. When epoxies are present, the diamines may react with either the epoxy or maleimide groups.

The composition may additionally contain an accelerator to increase the rate of cure of the epoxy plus amine reaction. These additives may also be used to increase the degree of cure of an epoxy resin in the absence of an amine hardener.

Accelerators which may be used herein include Lewis acids; amine complexes, such as BF$_3$.monoethylamine, BF$_3$.piperdine, BF$_3$.2-methylimidazole; amines, such as imidazole and its derivatives, such as 4-ethyl-2-methylimidazole, 1-methylimidazole, 2-methylimidazole; N,N-dimethylbenzylamine; acid salts of tertiary amines, such as the p-toluene sulfonic acid-:imidazole complex, salts of trifluoro methane sulfonic acid, such as FC-520 (obtained from 3M Company), organophosphonium halides and dicyandiamide. If used, the accelerator may be from 1 to 6 percent by weight of the epoxy component.

The composition may also contain compounds with one or more cyanate ester groups.

By cyanate ester is meant a compound having at least one cyanate group in its molecule. The cyanate ester is represented by the formula $$R-(O-C\equiv N)_m$$

wherein R is a residue derived from an aromatic hydrocarbon selected from the group consisting of benzene, biphenyl and naphthalene, or a residue derived from a compound in which at least two benzene rings are bonded to each other by a bridging member selected from the group consisting of

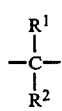

wherein $R^1$ and $R^2$ are the same or different and each represents a hydrogen atom or an alkyl group containing 1 to 4 carbon atoms,

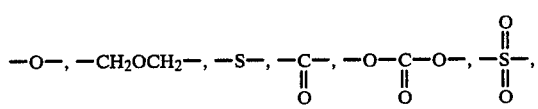

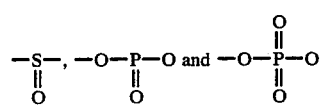

said aromatic nucleus is optionally substituted by a substituent selected from the group consisting of alkyl groups containing 1 to 4 carbon atoms, alkoxy groups containing 1 to 4 carbon atoms, chlorine and bromine; m is an integer of 1 to 5, and the cyanate group is always directly bonded to the aromatic nucleus.

Examples of the cyanate ester include cyanatobenzene, dicyanatobenzene;
1,3,5-tricyanatobenzene; 1,3-, 1,4-, 1,6-, 1,8-, 2,6- or 2,7-dicyanatonaphthalene;
1,3,6-tricyanatonaphthalene; 4,4'-dicyanatobiphenyl;
bis(4-cyanatophenyl)methane;
2,2-bis(4-cyanatophenyl)propane,
2,2-bis(3,5-dichloro-4-cyanatophenyl)propane,
2,2-bis(3,5-dibromo-4-dicyanatophenyl)propane;
bis(4-cyanatophenyl)ether;
bis(4-cyanatophenyl)thioether;
bix(4-cyanatophenyl)sulfone;
tris(4-cyanatophenyl)phosphite;
tris(4-cyanatophenyl)phosphate;
bis(3-chloro-4-cyanatophenyl)methane; cyanated novolak; cyanated bisphenol terminated polycarbonate or other thermoplastic oligomer; and mixtures thereof.

The above mentioned cyanate esters may be used as mixtures.

Prepolymers may be used containing a symmetrical triazine ring which is prepared by the trimerization of the cyanate groups of the cyanate ester, and which have an average molecular weight of at least 400 but no more than 6,000. Such prepolymers can be prepared by polymerizing the above cyanate esters in the presence of, as a catalyst, an acid such as a mineral acid or Lewis acid, a base such as sodium hydroxide, a sodium alcoholate or a tertiary amine, or a salt such as sodium carbonate or lithium chloride.

The cyanate ester can be used in the form of a mixture of the monomer and the prepolymer.

The compositions of this invention may optionally contain a thermoplastic polymer. These materials have beneficial effects on the viscosity and film strength characteristics of the bismaleimide/liquid coreactant mixture and may also have beneficial effects on the properties of reinforced composites made from these resins.

The thermoplastic polymers used in this invention include polyarylethers of formula XIII which are described in U.S. Pat. Nos. 4,108,837 and 4,175,175, $$-(O-R'-O-R'')_{\overline{n}} \qquad \text{XIII}$$

wherein R' is a residuum of a dihydric phenol such as bisphenol A, hydroquinone, resorcinol, 4,4-biphenol, 4,4'-dihydroxydiphenyl sulfone, 4,4'-dihydroxy-3,3' 5,5'-tetramethyldiphenyl sulfide, 4,4'-dihydroxy-3',3',5,5'-tetramethyldiphenyl sulfone and the like. R" is a residuum of a benzenoid compound susceptible to nucleophilic aromatic substitution reactions such as 4,4'-dichlorodiphenyl sulfone, 4,4'-difluorobenzophenone, and the like. The average value of n is from about 8 to about 120.

Other suitable polyarylethers are described in U.S. Pat. No. 3,332,209.

Also suitable are polyhydroxyethers of the formula:

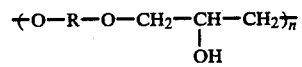

where R has the same meaning as for Formula XIII and the average value of n is between about 8 and about 300; and polycarbonates such as those based on bisphenol A, tetramethyl bisphenol A, 4,4'-dihydroxydiphenyl sulfone, 4,4'-dihydroxy-3,3',5,5'-tetramethyl-diphenyl sulfone, hydroquinone, resorcinol, 4,4'-dihydroxy- 3,3′,5,5′-tetramethyl diphenyl sulfide, 4,4′biphenol, 4,4′-dihydroxydiphenyl sulfide, phenolphthalein, 2,2,4,4-tetramethyl-1,3-cyclobutane diol, and the like. Other suitable thermoplastics include poly(ε-caprolactone); polybutadiene; polybutadiene/acrylonitrile copolymers, including those optionally containing epoxy, vinyl, acrylic, methacrylic, amine, carboxyl, hydroxy, or thiol groups; polyesters, such as poly(butylene terephthalate) and poly(ethylene terephthalate); polyetherimides such as the Ultem resins (obtained from the General Electric Company); acrylonitrile/butadiene/styrene copolymers; polyamides such as nylon 6, nylon 6,6, nylon 6,12, and Trogamid T (obtained from Dynamit Nobel Corporation); poly(amideimides) such as Torlon (obtained from Amoco Chemical Corporation, Napierville, IL); polyolefins; polyethylene oxide; poly(butyl methacrylate); impact-modified polystyrene; sulfonated polyethylene; polyarylates such as those derived from bisphenol A and isophthalic and terephthalic acid; poly(2,6-dimethyl phenylene oxide) and its copolymers; polyvinyl chloride and its copolymers; polyacetals; polyphenylene sulfide and the like.

Poly(vinyl acetate) and copolymers of vinyl acetate with other vinyl and acrylic monomers may also be used. Thermoplastics such as low profile additives, for example, LP-40A, may also be used.

Also suitable are vinyl methyl or vinyl phenyl silicone rubbers such as polymers of the formula —$R_2$SiO— wherein up to 10% of the R groups are vinyl, the remainder being either methyl and/or phenyl.

Particularly suitable are rubber modifiers, such as butadiene polymers and butadiene/acrylonitrile copolymers including those optionally containing terminal and/or pendent amine, epoxy, carboxyl, hydroxyl, thiol, or unsaturated double bond groups, such as acrylates or methacrylates or vinyls. These are exemplified by the Hycar Reactive Liquid Polymers available from B. F. Goodrich, the 1,2-polybutadiene resins available from Nippon Soda Co., the polybutadiene resins available from Arco Chemical Co. (as poly-BD resins) and others. Elastomers such as ethylene/acrylic copolymers, exemplified by the Vamac resins available from duPont, and other elastomeric polymers and copolymers may also be used.

The preferred thermoplastics include polysulfones, phenoxy resins, and polyarylates and the butadiene/acrylonitrile copolymers described above.

The structural fibers which are useful in this invention include carbon, graphite, glass, silicon carbide, poly(benzothiazole), poly(benzimidazole), poly(benzoxazole), aluminum, titanium, boron, and aromatic polyamide fibers. These fibers are characterized by a tensile strength of greater than 100,000 psi, a tensile modulus of greater than two million psi, and a decomposition temperature of greater than 200° C. The fibers may be used in the form of continuous tows (1000 to 400,000 filaments each), woven cloth, whishers, chopped fiber or random mat. The preferred fibers are carbon fibers, aromatic polyamide fibers, such as Kevlar 49 fiber (obtained from E. I. duPont de Nemours, Inc., Wilmington, DE), and silicon carbide fibers.

The compositions of component ii contains 1 to 99 weight percent, preferably 20–98 percent of the bismaleimide; 1 to about 60 percent, preferably 3 to 40 percent of the liquid coreactant or mixture of coreactants comprising molecules with one or more amino, epoxy, cyanate, vinyl groups such as —CH=$CH_2$, >C=$CH_2$, or —CH=CH— and other functionalities as described above, and 1 to about 40 percent, preferably 2 to 30 percent of other additives, such as thermoplastic polymers and other coreactants.

Additional components in the composition include initiators for vinyl polymerization such as di-t-butyl peroxide, dicumyl peroxide, 1,1-bis(t-butylperoxy)cyclohexane, azo bis-(isobutyronitrile), t-butyl perbenzoate, and the like. The initiator comprises from 0 to 3 percent by weight of the total composition.

Inhibitors for vinyl polymerizations may also be used. They include, hydroquinone, t-butyl hydroquinone, benzoquinone, p-methoxyphenol, and 4-nitro-m-cresol. Inhibitors are present in amounts of from 0 to 2 percent by weight of the total composition.

When a structural fiber is used, the amount of fiber in the total composition is between about 10 and about 90 percent by weight, preferably between about 20 to about 85 percent by weight.

Preimpregnated reinforcement may be made from the compositions of this invention by combining component ii with a structural fiber.

Preimpregnated reinforcement may be prepared by several techniques known in the art such as wet winding or hot melt. In one method of making impregnated tow or undirectional tape, the fiber is passed into a bath of the resin mixture. A non-reactive, volatile solvent such as methyl ethyl ketone may be optionally included in the resin bath to reduce viscosity. After impregnation, the reinforcement is passed through a die to remove excess resin, sandwiched between plies of release paper, passed through a set of heated rollers, cooled, and taken up on a spool. It is used within a few days or may be stored for months at 0° F.

Composites may be prepared by curing the preimpregnated reinforcement using heat and optionally pressure. Vacuum bag/autoclave cures work well with these compositions. Laminates may also be prepared via wet layup followed by compression molding, resin transfer molding, or by resin injection, as described in European Patent Application No. 0019149 published Nov. 26, 1980. Typical cure temperatures are 100° F. to 600° F., preferably 180° F. to 490° F.

The compositions of this invention may also be used for filament winding. In this composite fabrication process, continuous reinforcement in the form of tape or tow—either previously impregnated with resin or impregnated during winding—is placed over a rotating and removable form or mandrel in a previously determined pattern. Generally the shape is a surface of revolution and contains end closures. When the proper number of layers are applied, the wound form is cured in an oven or autoclave and the mandrel removed.

Tacky drapable prepreg can be obtained with a wide variety of compositions. Long prepreg shelf lives can be obtained—typically one to four weeks.

The compositions of this invention may be used as matrix resins for composites, high temperature coatings, and adhesives. When reinforced with structural fibers, they may be used as aircraft parts such as wing skins, wing-to-body fairings, floor panels, flaps, radomes; as automotive parts, such as driveshafts, bumpers, and springs; and as pressure vessels, tanks and pipes. They are also suitable for protective armor on military vehicles and sporting goods applications such as golf shafts, tennis rackets, and fishing rods.

In addition to structural fibers, the composition may also contain particulate fillers such as talc, mica, calcium carbonate, aluminum trihydrate, glass microballoons, phenolic thermospheres, and carbon black. Up to half of the weight structural fiber in the composition may be replaced by filler. Thixotropic agents such as fumed silica may also be used.

EXAMPLES

The following examples serve to give specific illustrations of the practice of this invention but they are not intended in any way to limit the scope of this invention.

EXAMPLE 1

Preparation of the bismaleimide of formula III $\alpha,\alpha'$-Bis(4-maleimidophenyl)-meta-diisopropylbenzene A 3 L 4-neck flask equipped with an overhead stirrer, a nitrogen gas dispersion tube and outlet, an addition funnel, and a thermometer with a temperature controller was charged with 444 ml acetone and 98.2 g maleic anhydride. The mixture was stirred to dissolve the maleic anhydride and sparged with nitrogen for 15 minutes. A solution of 150 g of $\alpha,\alpha'$-bis(4-aminophenyl)-meta-diisopropylbenzene in 444 ml acetone was added over 30 minutes during which time the reaction mixture formed an opaque, light yellow slurry. The slurry was stirred and heated at 40° C. for one hour.

The reaction mixture was then charged with 4.7 g of $MgCl_2.6H_2O$, 23 ml triethylamine, and 238 g of acetic anhydride which was added over 15 minutes. Stirring and heating at 40° C. were continued for three hours and then the heat was turned off while stirring continued for 16 hours. About 20 minutes after the end of the acetic anhydride addition, the slurry changed to a clear gold solution which grew darker with time.

After diluting the reaction mixture with 600 ml of dichloromethane, it was washed (12 L separatory flask) with 5×1 L of 0.25M potassium carbonate, once with dilute brine, twice with water and again with brine. The methylene chloride solvent was then removed under vacuum and the residue was taken up in 4 L of acetone and then coagulated in 9 to 10 parts water per portion of acetone solution. The precipitate was collected and dried in an oven under vacuum. Over a period of two days the oven heat was gradually increased until the material formed a brittle melt ($\approx 70°$ C.).

The proton NMR was consistent with the expected structure. LC analysis showed one major product with two minor impurities.

EXAMPLE 2

Preparation of the Bismaleimide of Formula IV $\alpha,\alpha'$-Bis(4-maleimidophenyl)para-diisopropylbenzene A 5 L 4-neck flask equipped with an overhead stirrer, a nitrogen gas dispersion tube and outlet, an addition funnel, and a thermometer with a temperature controller was charged with 880 ml acetone and 166.7 g maleic anhydride. The mixture was stirred to dissolve the maleic anhydride and then sparged with nitrogen for 15 minutes. A solution of 250 g of $\alpha,\alpha'$-Bis(4-aminophenyl)para-diisopropylbenzene in 1680 ml acetone was added over 30 minutes during which time the reaction mixture formed an opaque yellow slurry. The slurry was stirred and heated at 40° C. for one hour.

The reaction was then charged with 8.03 g of $MgCl_2.6H_2O$, 39 ml triethylamine, and 404 g of acetic anhydride which was added over 15 minutes. Stirring and heating at 40° C. were continued for about 20 hours during which time the slurry changed to green-brown and then to an off-white color. The mixture was diluted with 4.8 L of dichloromethane and then washed (12 L separatory flask) with 7×2 L of 0.25M potassium carbonate. Salt was added to some washes to improve phase separation. After 2 additional 2 L washs with water, the organic phase was coagulated in 10 parts of isopropanol. The precipitate, a fine yellow powder, was collected and dried at $\approx 60°$ C. under vacuum. The dried product (238 g) had a melting point of about 246° C. The proton NMR was consistent with the expected structure. LC analysis showed one major product with two minor impurities.

EXAMPLE 3

Preparation of Bismaleimide/Coreactant Casting

A mixture of 6.2 g of the bismaleimide from Example 1 and 3.8 g of o,o'-diallylbisphenol A was blended in a 25 ml flask on a rotary evaporator at 125° C. for 10 minutes to form a transparent gold solution. This was poured into a small casting frame ($\approx 4'' \times 4''$ glass plates with a 1/16" Teflon spacer frame) and cured with the following schedule.

The casting was cured by heating from 25° C. to 79° C. at 1.5° C./min.; holding at 79° C. for 2 hours; heating from 79° C. to 177° C. at 1.5° C./min.; holding at 177° C. for 4 hours, heating to 246° C. at 1° C./min.; holding at 246° C. for 4 hours; and then cooling to room temperature at 1.5° C./min.

Other cure schedules could also be used having shorter or longer hold periods at these or other temperatures.

The transparent, dark gold casting was cut into DMA (dynamic mechanical analysis) test specimens which showed a Tg of 237° C. when tested at a heating rate of 5°/minute. After soaking in water at 160° F. for two weeks, the casting samples absorbed 2.2% water.

Similar results were obtained with cure schedule of Example 4.

EXAMPLE 4

Preparation of Bismaleimide/Coreactant Casting

A mixture of 5.0 g of the bismaleimide from Example 2 and 5.0 g of o,o'-diallylbisphenol A was blended in a 25 ml flask on a rotary evaporator at 140° C. for about 15 minutes and then poured into a small frame as in Example 3 and cured with the following schedule.

The casting was cured by heating from 25° C. to 100° C. at 1°/min., holding at 100° C. for 1 hour, heating from 100° C. to 180° C. at 1°/min., holding at 180° C. for 3 hours, heating from 180° C. to 240° C. at 1°/min., holding at 240° C. for 5 hours and cooling to room temperature at 3°/min.

The transparent, dark casting was evaluated as in Example 3 and showed a Tg of 227° C. and a water absorption of 2.2%.

Control Examples

Control examples prepared in a similar manner showed the above castings to exhibit a low level of water absorption relative to that found with lower molecular weight (i.e., 2 aromatic rings) bismaleimides. For example, a casting prepared from 5.4 parts methylene dianiline bismaleimide and 4.6 parts diallylbisphenol A had a Tg of 285° C. and absorbed 3.7% water. A similar casting containing oxydianiline bismaleimide had a Tg of 280° C. and absorbed 3.9% water.

Controls also showed significantly lower Tg values when higher molecular weight (i.e., four aromatic rings) bismaleimides were used. For example, a casting based on 6.6 parts of 4,4'-bis(3-maleimidophenoxy)-diphenylsulfone had a Tg of only 213° C. even after post-curing at 275° C. for 3 hours. This casting had a water absorption of 1.9%.

The data from Examples 3, 4 and the Control Examples are set forth in Table I below.

TABLE I

| | Comparative Properties of Multi-ring Bismaleimides | | | | |
|---|---|---|---|---|---|
| BMI | Weight BMI | Rings in BMI | Weight Diluent[f] | Tg (°C.) | $H_2O$ Absorbed[g] |
| MDA[a] | 5.4 | 2 | 4.6 | 285 | 3.7 |
| ODA[b] | 5.4 | 2 | 4.6 | 280 | 3.9 |
| BAM[c] | 6.2 | 3 | 3.8 | 237 | 2.2 |
| BAP[d] | 5.0 | 3 | 5.0 | 227 | 2.2 |
| SED-M[e] | 6.6 | 4 | 3.4 | 213 | 1.9 |

[a]Methylene dianiline bismaleimide.
[b]Oxydianiline bismaleimide.
[c]α,α'-Bis(4-maleimidediphenyl)-meta-diisopropylbenzene.
[d]α,α'-Bis(4-maleimidophenyl)-para-diisopropylbenzene.
[e]4,4'-Bis(3-maleimidophenoxy)diphenylsulfone
[f]o,o'-diallyl bisphenol A
[g]2 weeks in 160° F. water.

It is evident from the data set forth in Table I that bismaleimides containing three aromatic rings provide formulations with lower water absorption than bismaleimides continuing two aromatic rings and also higher Tg values than bismaleimides having four aromatic rings. Such a balance of properties is desirable.

EXAMPLE 5

Prepreg Composition

A carbon fiber prepreg is prepared from the resin of Example 4 by coating the resin on release paper at elevated temperatures to provide a suitable viscosity and contacting two plies of the coated paper with a ribbon of carbon fiber tows in a prepreg machine. In the prepreg machine, the sandwich of fiber and coated release paper is passed over a series of heated rollers to melt the resin into the fibers. The fiber is a polyacrylonitrile-based fiber customarily used in the preparation of high performance carbon fiber composites.

Although the invention has been illustrated by the foregoing examples, it is not to be construed as being limited to the materials employed therein, but rather, the invention relates to the generic area as hereinbefore disclosed. Various modifications and embodiments thereof can be made without departing from the spirit and scope thereof.

What is claimed is:

1. A bismaleimide of the formula:

[Formula II: bismaleimide structure with R, N, C=O groups, phenyl rings with $(R_1)_n$ substituents, $R_2$ groups, and Ar bridge]

wherein Ar is selected from the group consisting of a single aromatic nucleus, a fused aromatic nucleus, a single aromatic nucleus containing one or more R or $R_1$ groups, and a fused aromatic nucleus containing one or more R or $R_1$ groups; R and $R_1$ individually represent alkyl or halogen groups; $R_2$ represents an alkyl group of from 1 to 12 carbon atoms; and n has a value of from 0 to 4.

2. A bismaleimide as defined in claim 1 where Ar is phenylene, and R and $R_1$ are hydrogen.

3. A bismaleimide as defined in claim 1 where Ar is meta-phenylene.

4. A bismaleimide as defined in claim 1 where Ar is para-phenylene.

5. A bismaleimide as defined in claim 1 of the following formula:

[Formula III: bismaleimide structure with $CH_3$ groups]

6. A bismaleimide as defined in claim 1 of the following formula:

[Formula IV: bismaleimide structure with $CH_3$ groups]

7. A bismaleimide of the formula:

[Formula II: bismaleimide structure]

wherein Ar is selected from the group consisting of a single aromatic nucleus, a fused aromatic nucleus, a single aromatic nucleus containing one or more R or $R_1$ groups, and a fused aromatic nucleus containing one or more R or $R_1$ groups; R and $R_1$ individually represent alkyl or halogen groups; $R_2$ represents an alkyl group of from 1 to 12 carbon atoms; and n has a value of from 0 to 4 in which up to 50% of the maleimide or substituted maleimide groups have been replaced by the following terminal imide groups:

[succinimide and methyl-substituted succinimide structures]

succinimide, phthalimide, and substituted succinimide, and phthalimide.

8. A bismaleimide mixture consisting of a mixture of the bismaleimides of claim 3 and claim 4.

9. A bismaleimide mixture which consists of a mixture of the bismaleimides of claim 5 and claim 6.

10. A prepregable resin composition comprising the bismaleimide of claim 1 and one or more liquid coreactants.

* * * * *